US012789187B2

(12) United States Patent
Paust et al.

(10) Patent No.: US 12,789,187 B2
(45) Date of Patent: Nov. 10, 2026

(54) ISOLATING ANALYTES OF DIFFERENT ANALYTE CLASSES

(71) Applicant: Hahn-Schickard-Gesellschaft fuer angewandte Forschung e.V., Villingen-Schwenningen (DE)

(72) Inventors: Nils Paust, Freiburg im Breisgau (DE); Peter Juelg, Freiburg (DE); Jan Lueddecke, Neuenburg am Rhein (DE); Tobias Hutzenlaub, Ettenheim (DE); Franziska Schlenker, Kenzingen (DE); Ehsan Mahmodi Arjmand, Freiburg (DE); Gustav Grether, Muehlheim (DE); Marc Karle, Auggen (DE)

(73) Assignee: Hahn-Schickard-Gesellschaft fuer angewandte Forschung e.V., Villingen-Schwenningen (DE)

( * ) Notice: Subject to any disclaimer, the term of this patent is extended or adjusted under 35 U.S.C. 154(b) by 419 days.

(21) Appl. No.: 18/440,734

(22) Filed: Feb. 13, 2024

(65) Prior Publication Data

US 2024/0181456 A1 Jun. 6, 2024

Related U.S. Application Data

(63) Continuation of application No. PCT/EP2022/072377, filed on Aug. 9, 2022.

(30) Foreign Application Priority Data

Aug. 13, 2021 (DE) ........................ 102021208893.7

(51) Int. Cl.

*B01L 3/00* (2006.01)
*B03C 1/01* (2006.01)

(Continued)

(52) U.S. Cl.

CPC .......... *B01L 3/502753* (2013.01); *B03C 1/01* (2013.01); *B03C 1/30* (2013.01);

(Continued)

(58) Field of Classification Search

CPC ....... B01L 3/502753; B01L 2200/0631; B01L 2200/0647; B01L 2300/0681;

(Continued)

(56) References Cited

U.S. PATENT DOCUMENTS

| | | | |
|---|---|---|---|
| 10,808,240 | B2 | 10/2020 | Stoll et al. |
| 2014/0030788 | A1 | 1/2014 | Chen et al. |

(Continued)

FOREIGN PATENT DOCUMENTS

| | | | |
|---|---|---|---|
| CN | 106662596 | A | 5/2017 |
| DE | 102018219091 | A1 | 5/2020 |

(Continued)

OTHER PUBLICATIONS

C.-J. Kim et al., "Fully automated, on-site isolation of cfDNA from whole blood for cancer therapy monitoring", Lab on a chip 18, 1320 (2018), pp. 1320-1329.

(Continued)

*Primary Examiner* — Benjamin R Whatley

(74) *Attorney, Agent, or Firm* — Ashurst Perkins Coie US LLP; Michael A. Glenn

(57) ABSTRACT

In a method for isolating analytes of a first analyte class, which are extracellular vesicles and/or circulating tumor cells, and analytes of a second analyte class, which are cell-free nucleic acids, from the same sample volume of a biological sample in a centrifugal microfluidic system, the sample volume is guided into a first isolation chamber of a fluidics module containing a first isolation structure so that the analytes of the first analyte class are retained by the first isolation structure while the analytes of the second analyte (Continued)

class are not retained and pass through the first isolation structure as part of a residual liquid, which is passed into a second isolation chamber of the fluidics module containing a second isolation structure so that the analytes of the second analyte class are retained by the second isolation structure. The analytes of the first analyte class and the second analyte class are separated from the respective isolation structure to provide the analytes for subsequent analysis.

11 Claims, 5 Drawing Sheets

(51) Int. Cl.

| | |
|---|---|
| ***B03C 1/30*** | (2006.01) |
| *C12N 15/10* | (2006.01) |
| *G01N 1/40* | (2006.01) |

(52) U.S. Cl.

CPC .................. *B01L 2200/0631* (2013.01); *B01L 2200/0647* (2013.01); *B01L 2300/0681* (2013.01); *B01L 2300/0864* (2013.01); *B01L 2400/0409* (2013.01); *B01L 2400/043* (2013.01); *B03C 2201/18* (2013.01); *B03C 2201/26* (2013.01); *C12N 15/1013* (2013.01); *G01N 1/4077* (2013.01)

(58) Field of Classification Search

CPC ..... B01L 2300/0864; B01L 2400/0409; B01L 2400/043; B01L 2300/0803; B03C 1/01; B03C 1/30; B03C 2201/18; B03C 2201/26; C12N 15/1013; G01N 1/4077; B01F 33/451

See application file for complete search history.

(56) References Cited

U.S. PATENT DOCUMENTS

| | | | | |
|---|---|---|---|---|
| 2017/0168046 | A1 | 6/2017 | Saiki et al. | |
| 2019/0201900 | A1 | 7/2019 | Shachar et al. | |
| 2021/0252515 | A1 | 8/2021 | Hin et al. | |
| 2023/0109130 | A1 * | 4/2023 | Duffy ................. | G01N 33/6869 435/7.92 |

FOREIGN PATENT DOCUMENTS

| | | | |
|---|---|---|---|
| EP | 2245458 | B1 | 10/2016 |
| EP | 3167062 | B1 | 10/2019 |
| WO | 2017197399 | A1 | 11/2017 |

OTHER PUBLICATIONS

H.-K. Woo et al., "Exodisc for Rapid, Size-Selective, and Efficient Isolation and Analysis of Nanoscale Extracellular Vesicles from Biological Samples", ACS nano 11, 1360 (2017), pp. 1360-1370, XP055948413.

J.L. Garcia-Cordero et al., "Microfluidic systems for cancer diagnostics", Curr. Opin. Biotechnol. (2020) 65:37-44.

Shu Zhu et al. "Microfluidics for label-free sorting of rare circulating tumor cells", Analyst, UK, vol. 145, No. 22, Jan. 1, 2020 (Jan. 1, 2020), pp. 7103-7124, XP055750399.

Wang Wenshuo et al., "Recent Progress in Isolation and Detection of Extracellular Vesicles for Cancer Diagnostics", Advanced Healthcare Materials, DE, vol. 7, No. 20, Oct. 1, 2018 (Oct. 1, 2018), XP055974247—27 pages.

* cited by examiner

ISOLATING ANALYTES OF DIFFERENT ANALYTE CLASSES

CROSS-REFERENCE TO RELATED APPLICATIONS

This application is a continuation of copending International Application No. PCT/EP2022/072377, filed Aug. 9, 2022, which is incorporated herein by reference in its entirety, and additionally claims priority from German Application No. 102021208893.7, filed Aug. 13, 2021, which is also incorporated herein by reference in its entirety.

TECHNICAL FIELD

The present invention relates to methods and devices for isolating different analyte classes from the same sample volume and, in particular, to methods and devices for isolating extracellular vesicles, EVs, and/or circulating tumor cells as a first analyte class, and cell-free nucleic acids as a second analyte class from the same sample volume of a biological sample.

BACKGROUND OF THE INVENTION

Early diagnosis of diseases is often crucial for patients' chances of recovery, which is why there is an urgent need for high diagnostic sensitivity. In addition, a specific diagnosis of diseases is relevant in order to make the right treatment decisions and to minimize false-positive findings, as these are associated with a great burden for patients and high additional costs for the healthcare system due to follow-up examinations.

Consequently, in addition to high sensitivity, there is need for high diagnostic specificity. The sensitivity and specificity of a diagnostic test are defined by determining a common threshold value, which divides test results into positive and negative. This means that sensitivity and specificity are linked to each other and cannot be optimized independently of each other as long as the diagnosis is based on a single analyte.

A promising way of increasing both diagnostic sensitivity and specificity is the analysis of several analytes or analyte classes in one patient sample and at one point in time. However, this usually entails either dividing the patient sample into several sub-volumes or collecting larger sample volumes, which not only incurs costs, e.g. several blood tubes, but also increases the burden for the patient. This problem is increased by the fact that with the disease-associated analytes known today from non-invasive or minimally invasive samples, a very large amount of sample is collected anyway, e.g. 10 mL of whole blood for the analysis of cfDNA (cell-free deoxyribonucleic acid) in plasma, which is burdensome for patients. The background to this is the often very low concentration of analytes within the sample matrix, particularly in the early stages of the disease or following therapy (monitoring of minimal residual disease, MRD).

For example, centrifugal microfluidic systems can be used to provide analytes for analysis from a biological sample and/or to analyze analytes. A centrifugal microfluidic system here is a system configured to handle liquids while utilizing the centrifugal force generated during rotation. Centrifugal microfluidics deals with handling liquids in the picoliter to milliliter range in rotating systems. Such systems are usually disposable polymer cartridges which are used in or instead of centrifuge rotors, with the intention of automating laboratory processes. Standard laboratory processes such as pipetting, centrifugation, mixing or aliquoting can be implemented in a microfluidic cartridge. For this purpose, the cartridges contain channels for fluid guidance and chambers for collecting liquids. In general, such structures designed to handle fluids may be referred to as fluidics structures. In general, such cartridges may be referred to as fluidics modules.

The cartridges can be subjected to a predefined sequence of rotational frequencies, the frequency protocol, so that the liquids in the cartridges can be moved by the centrifugal force. Centrifugal microfluidics is mainly used in laboratory analysis and mobile diagnostics.

Methods and devices for isolating analytes from biological samples using centrifugal microfluidic systems are known.

Chi-Ju Kim et al, "Fully automated, on-site isolation of cfDNA from whole blood for cancer therapy monitoring", Lab Chip, 2018, 18, pages 1321 to 1329, disclose a centrifugal microfluidic chip and an associated apparatus which can be used to isolate cfDNA from whole blood fully automatically and in less than 30 minutes. The cfDNA is bound to silica beads, washed and eluted. The fluidics are based on membrane valves which are opened or closed by a plunger.

Hyun-Kyung Woo et al, "Exodisc for Rapid, Size-Selective, and Efficient Isolation and Analysis of Nanoscale Extracellular Vesicles from Biological Sample", ACS Nano 2017, 11, pages 1360 to 1370, disclose a fluidics module in the form of a disc having fluidics structures to isolate EVs, extracellular vesicles, by means of centrifugal microfluidics. Two nanofilters are provided in the fluidics module, by means of which EVs in the size range from 20 nm to 600 nm are isolated from biological samples within 30 minutes. At first, large particles are removed from the sample using a first filter and then EVs are isolated using a second filter. The EVs are then washed and eluted. The fluidics are based on membrane valves which are opened or closed by a plunger.

There are also methods in which two or more analyte classes are isolated from a single sample.

A method is known from EP 3 167 062 B1 in which particles, cells and/or cell pieces or other impurities are removed from a biological sample by centrifugation or filtration before microvesicles are isolated and purified and/or enriched. High-quality nucleic acids were then extracted from the microvesicles. In the method described, a biological sample is provided and brought into contact with a capture surface, under conditions sufficient to obtain cell-free DNA (deoxyribonucleic acid) and microvesicles from the biological sample on or in the capture surface. The capture surface is contacted with a phenol-based lysis reagent while cell-free DNA and the microvesicles are located on or in the capture surface, thereby releasing DNA and RNA (ribonucleic acids) from the sample and producing a homogenate. DNA, RNA or both DNA and RNA are then extracted from the homogenate.

A similar method for isolating extracellular vesicles and co-isolating cell-free DNA from bio-liquids is known from U.S. Pat. No. 10,808,240 B2. A biological sample is contacted with a solid capture surface under conditions sufficient to retain cell-free DNA and microvesicles from the biological sample on or in the capture surface. The capture surface is contacted with a GTC-based elution buffer while cell-free DNA and the microvesicles are located on or in the capture surface, thereby releasing the DNA and RNA from the sample and producing a homogenate. The DNA, the RNA, or both the DNA and the RNA are extracted from the homogenate.

A method is also known from EP 2 245 458 B1 in which a homogenate is produced which consists of DNA from extracellular vesicles and cfDNA.

It has been recognized that a major disadvantage of the methods known in known technology is that, after these methods have been carried out, the EV DNA and cfDNA (additionally RNA, depending on the method) are present as a homogenate and cannot be analyzed in a differentiated manner. The extracellular vesicles are destroyed, i.e. characteristics such as surface markers, size distribution etc. cannot be analyzed further. Extracellular vesicles contain other relevant analytes (e.g. proteins). These are lost in the known methods in which a homogenate is produced. The amount of cfDNA already represents a biomarker. This quantity is falsified by additional EV-DNA.

It has also been recognized that a remedy could be provided by analyzing different analyte classes from the identical sample volume, wherein several different analytes can increase the diagnostic sensitivity/specificity, but this has so far entailed a large sample volume. Advantageously, the used methods for pre-analytical isolation of the different analyte classes are to be compatible with one another and be able to be combined in an integrated, automated process chain. This could offer an economically attractive solution, as high costs due to manual intermediate steps and the need for several different laboratory apparatus for isolation could be avoided. At present, there is no method which makes it possible to isolate several analyte classes from an identical sample volume and in a single integrated process chain, as the existing methods would either influence/interfere with one another and/or be based on different principles that cannot be easily combined in one laboratory apparatus.

It is the object of the invention to provide methods and devices which enable analytes of different analyte classes, namely extracellular vesicles and/or circulating tumor cells on the one hand and cell-free nucleic acids on the other hand, to be isolated from the same sample volume in a way which allows implementation in an integrated process chain.

SUMMARY

According to an embodiment, a method for isolating analytes of a first analyte class, which are extracellular vesicles and/or circulating tumor cells, and analytes of a second analyte class, which are cell-free nucleic acids, from the same sample volume of a biological sample in a centrifugal microfluidic system, having a fluidics module having a first isolation chamber containing a first isolation structure and a second isolation chamber containing a second isolation structure, may have the steps of: guiding the sample volume into the first isolation chamber so that the analytes of the first analyte class are retained by the first isolation structure, while the analytes of the second analyte class are not retained by the first isolation structure and pass through the first isolation structure as part of a residual liquid; guiding the residual liquid into the second isolation chamber so that the analytes of the second analyte class are retained by the second isolation structure; and separating the analytes of the first analyte class from the first isolation structure and separating the analytes of the second analyte class from the second isolation structure to provide the analytes of the first analyte class and the analytes of the second analyte class separately from each other for subsequent analysis, wherein the first isolation structure is a filter having a pore size in a range from 20 nanometers to 200 nanometers, advantageously in a range from 20 nanometers to 45 nanometers, wherein the second isolation structure is a surface for binding analytes, wherein the surface is formed by particles, and wherein the particles are magnetizable, the method having rotating the fluidics module to, by means of one or more stationary or movable magnets of a processing apparatus, move the magnetizable particles in the second isolation chamber to assist mixing of the particles with the residual liquid, and/or support retaining the magnetizable particles in the second isolation chamber during transfer of analytes of the second analyte class into the second collection chamber.

Another embodiment may have a centrifugal microfluidic device having a fluidics module for isolating analytes of a first analyte class, which are extracellular vesicles and/or circulating tumor cells, and analytes of a second analyte class, which are cell-free nucleic acids, from the same sample volume of a biological sample in a centrifugal microfluidic system, and a processing apparatus configured to subject the fluidics module to rotation, the fluidics module having: a first isolation chamber containing a first isolation structure; a second isolation chamber containing a second isolation structure; a first fluid line for guiding the sample volume into the first isolation chamber so that the analytes of the first analyte class are retained by the first isolation structure, while the analytes of the second analyte class are not retained by the first isolation structure and pass through the first isolation structure as part of a residual liquid; a second fluid line for guiding the residual liquid into the second isolation chamber so that the analytes of the second analyte class are retained by the second isolation structure; a first collection chamber connected to the first isolation chamber for receiving analytes of the first analyte class detached from the first isolation structure; and a second collection chamber connected to the second isolation chamber for receiving analytes of the second analyte class detached from the second isolation structure or for receiving the second isolation structure from which the analytes of the second analyte class have been detached, wherein the first isolation structure is a filter having a pore size in a range from 20 nanometers to 200 nanometers, advantageously in a range from 20 nanometers to 45 nanometers, wherein the second isolation structure is a surface for binding analytes, and wherein the surface is formed by magnetizable particles, wherein the processing apparatus has one or more stationary or movable magnets which are arranged outside the second isolation chamber in order to support mixing of magnetizable particles with the filtrate during rotation of the fluidics module and/or in order to support retention of the magnetizable particles in the second isolation chamber during transfer of analytes of the second analyte class into the second collection chamber.

Examples of the disclosure provide methods for isolating analytes of a first analyte class, which are extracellular vesicles and/or circulating tumor cells, and analytes of a second analyte class, which are cell-free nucleic acids, from the same sample volume of a biological sample in a centrifugal microfluidic system comprising a fluidics module having a first isolation chamber containing a first isolation structure, and a second isolation chamber containing a second isolation structure. The sample volume is guided into the first isolation chamber so that the analytes of the first analyte class are retained by the first isolation structure, while the analytes of the second analyte class are not retained by the first isolation structure and pass through the first isolation structure as part of a residual liquid. The residual liquid is guided into the second isolation chamber so that the analytes of the second analyte class are retained by the second isolation structure. The analytes of the first analyte class are separated from the first isolation structure and the analytes of the second analyte class are separated from the second isolation structure to provide the analytes of the first analyte class and the analytes of the second analyte class separately from each other for subsequent analysis.

Examples of the disclosure provide a fluidics module for isolating analytes of a first analyte class, which are extracellular vesicles and/or circulating tumor cells, and analytes of a second analyte class, which are cell-free nucleic acids, from the same sample volume of a biological sample in a centrifugal microfluidic system. The fluidics module comprises a first isolation chamber containing a first isolation structure, a second isolation chamber containing a second isolation structure, a first fluid line, a second fluid line, a first collection chamber, and a second collection chamber. The first fluid line is configured to guide the sample volume into the first isolation chamber so that the analytes of the first analyte class are retained by the first isolation structure, while the analytes of the second analyte class are not retained by the first isolation structure and pass through the first isolation structure as part of a residual liquid. The second fluid line is configured to guide the residual liquid into the second isolation chamber so that the analytes of the second analyte class are retained by the second isolation structure. The first collection chamber is connected to the first isolation chamber and is configured to receive analytes of the first analyte class detached from the first isolation structure. The second collection chamber is connected to the second isolation chamber and is configured to receive analytes of the second analyte class detached from the second isolation structure, or to receive the second isolation structure after the analytes of the second analyte class have been detached therefrom.

According to examples of the disclosure, analytes of different analyte classes are thus obtained from the same sample volume and provided separately from one another for further use thereof, for example an analysis or examination thereof. Since both analytes are recovered from the same sample volume, wherein the analytes of the second analyte class are recovered from the residual liquid remaining after isolation of the analytes of the first analyte class, isolation of both analyte classes from a small sample volume is possible. Furthermore, it has been recognized that it is possible to perform both isolations using a fluidics module in a centrifugal microfluidic system so that integration into a single process chain is possible.

BRIEF DESCRIPTION OF THE DRAWINGS

Embodiments of the invention are explained in more detail below with reference to the accompanying drawings, in which.

DETAILED DESCRIPTION OF THE INVENTION

Figure 1:
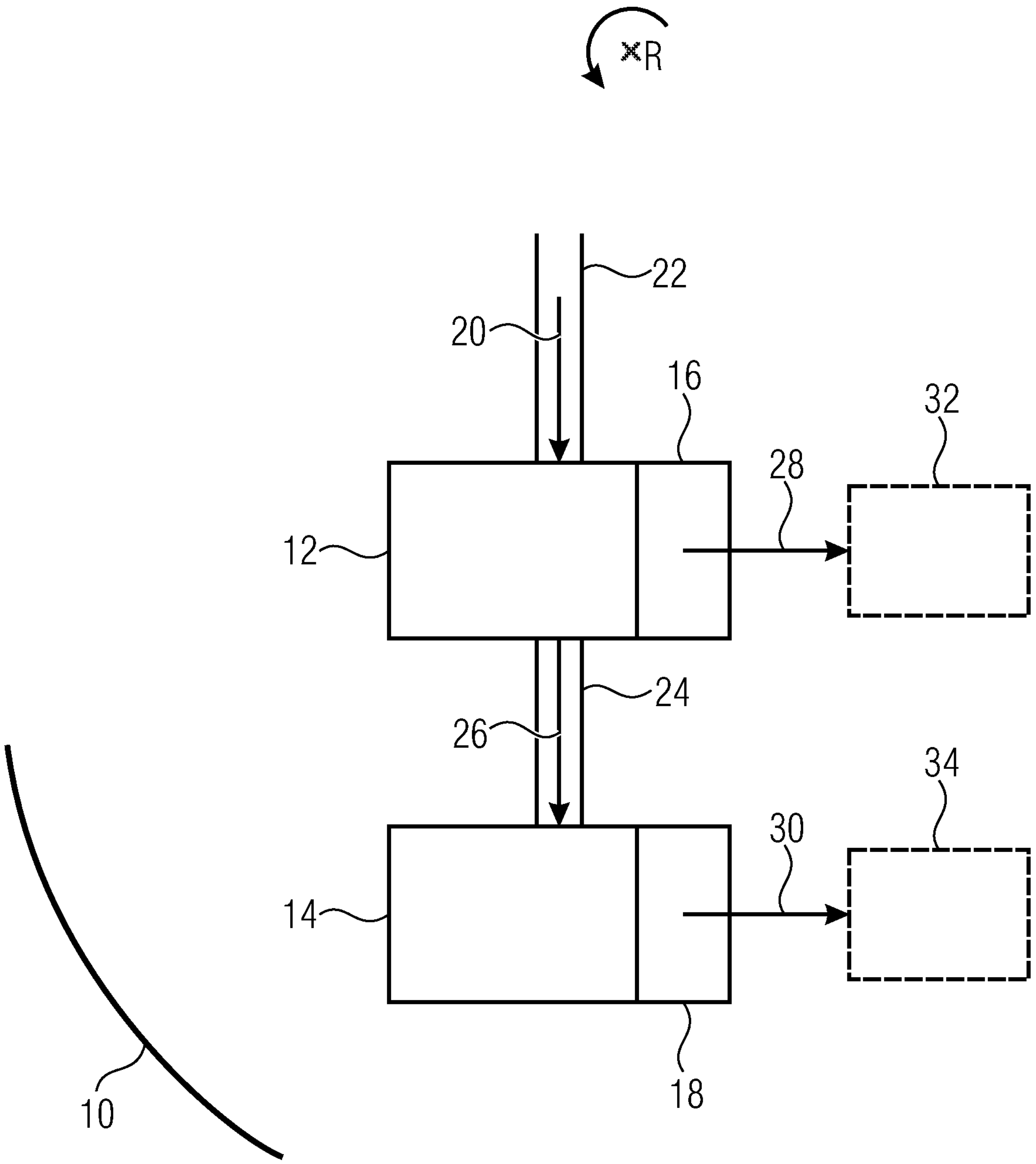
FIG. 1 shows a schematic representation of a fluidics module according to an example of the present disclosure.

In the following, examples of the present disclosure are described in detail using the accompanying drawings. It should be noted that identical elements or elements having the identical functionality are provided with identical or similar reference numerals, and a repeated description of elements provided with the identical or similar reference numerals is typically omitted. In particular, identical or similar elements may be provided with reference numerals having an identical number with a different or no lower case letter. Descriptions of elements having the identical or similar reference numerals may be interchangeable. In the following description, many details are described in order to provide a more thorough explanation of examples of the disclosure. However, it is apparent to those skilled in the art that other examples may be implemented without these specific details. Features of the various examples described may be combined with one another, unless features of a corresponding combination are mutually exclusive or such a combination is expressly excluded.

Before explaining examples of the present disclosure in more detail, definitions of some terms used herein are provided.

The term isolation is used herein to refer to methods aiming at removing the interfering components of a sample matrix, e.g. inhibitors or falsely analyzable components, and/or to increase the concentration of an analyte in a sample, e.g. by reducing the aqueous content of a sample. Isolation can be achieved either by enrichment of the analyte or by depletion of non-analyte substances. Synonymous terms for the term isolation are enrichment, extraction and purification.

In this context, a sample is a biological material which is usually taken from a person and is collected using a non-invasive or minimally invasive technique. The sample can be a liquid sample (e.g. whole blood, blood plasma, blood serum, urine, saliva, tear fluid, cerebrospinal fluid, seminal plasma) or a liquefied sample of solid origin (e.g. stool). This definition also includes samples generated on the basis of a human cell sample, e.g. a cell culture supernatant, even if the original cell sample was collected invasively.

A sample matrix refers to the components of a sample which are not to be analyzed. The matrix can make an analysis more difficult, e.g. if the analyte is only present in a very low concentration or if components of the matrix interfere with the analysis procedure.

Analytes are components to be analyzed. Analytes dissolved in the sample matrix include substances, molecules, particles, which can be analyzed in terms of number, concentration, biomarker signatures, etc. in an analysis procedure connected to isolation. Possible analytes in this context include nucleic acids, proteins, peptides, metabolites, secondary metabolites, vitamins, cells (human cells as well as fungi, bacteria or *mycoplasma*), exosomes and viruses.

The term analyte classes is used here to summarize those analytes which can be isolated using a single technical procedure. In this context, for example, DNA and RNA in their various forms are regarded as one analyte class, namely cell-free nucleic acids (cfNA). The heterogeneous subtypes of extracellular vesicles are also considered as one analyte class, namely extracellular vesicles (EV). This analyte class may further or alternatively include circulating tumor cells.

It should be noted that depending on the nature of the analyte of interest, for example small EV versus large EV, the parameters of the isolation procedure may vary, for example varying pore sizes in filtration. According to this definition, further analyte classes may be proteins, cells and cell fragments.

The term cell-free nucleic acids (cfNA) refers to various forms of DNA and RNA which occur outside of cells in the human body. Currently, this includes circulating cell-free DNA (ccfDNA) of both nuclear and mitochondrial origin, circulating tumor DNA (ctDNA), cell-free DNA (cfDNA), cellular DNA, circulating tumor RNA (ctRNA), microRNA (miRNA), and non-coding RNA (ncRNA).

The term extracellular vesicles (EV) refers to particles released by cells. They represent a heterogeneous population of different subtypes, which currently include exosomes, microvesicles, ectosomes and apoptotic corpuscles. The size of the particles varies between a few 10 nm and a few 1 μm, depending on the subtype. Various analytes, such as proteins, nucleic acids, lipids or metabolites, are found both inside the EV and partly on its surface.

Proteins are macromolecules consisting of amino acids linked by means of peptide bonds. They perform a wide variety of functions in the human body and are involved in a plurality of disease-associated processes. The analysis of cell-free proteins in a sample matrix, e.g. blood serum, can therefore be used for diagnostics alone or in combination with other analytes.

The term cells or cell fragments is used here to refer to all human blood cells (erythrocytes, leukocytes and thrombocytes), and other circulating (e.g. in the blood) or transported (e.g. in stool) cells. An example of circulating cells in the blood are circulating tumor cells (CTCs) or tumor-associated platelets (TEPs).

The term fluidics module is used here to refer to a module, for example a cartridge, having microfluidics structures configured to enable fluid handling as described herein. A centrifugal microfluidic fluidics module (cartridge) means a corresponding module which can be subjected to rotation, for example in the form of a fluidics module insertable into a rotational body, or a rotational body.

Examples of the invention can be used in particular in the field of centrifugal microfluidics, which involves the processing of liquids in the picoliter to milliliter range. Accordingly, the fluidic structures can have suitable dimensions in the micrometer range for handling corresponding liquid volumes.

If the term radial is used here, this means radial with respect to the center of rotation around which the fluidics module or the rotational body is rotatable. In the centrifugal field, a radial direction away from the center of rotation is therefore radially decreasing and a radial direction towards the center of rotation is radially increasing. A fluid channel whose beginning is closer to the center of rotation than its end, is therefore radially decreasing, while a fluid channel whose beginning is further away from the center of rotation than its end is radially increasing. A channel having a radially increasing section therefore has directional components which increase radially or run radially inwards. It is clear that such a channel does not have to run exactly along a radial line, but can run at an angle to the radial line or be curved.

Unless otherwise stated herein, room temperature (20° C.) is to be assumed for temperature-dependent variables.

Generally, examples of the present disclosure relate to methods and devices for purifying multiple analytes from a sample volume. Examples herein relate to a method for isolating multiple different classes of analytes, for example cell-free nucleic acids and extracellular vesicles, EVs in short, from a single sample volume, wherein the sample is typically from a human and collected by means of a non- or minimally invasive technique, for example blood, urine or stool. Examples make this possible without splitting the sample volume into multiple sub-volumes, as such a split would result in a loss in absolute analyte volume per analysis, which in turn results in a loss in achievable sensitivity. Furthermore, it is to be avoided that different analyte classes are isolated together to form a single isolate, since in this way the structurally identical components of the different analytes, for example the cell-free nucleic acids and the EV-associated nucleic acids, cannot be analyzed in a differentiated manner. A centrifugal microfluidic process chain was identified as a suitable method for avoiding sample splitting, which enables the isolation of several classes of analytes from the identical sample volume, wherein the individual isolation methods are compatible with each other and do not interfere with each other. In contrast to previous methods, which entail either splitting of the sample prior to isolation or multiple serial isolation procedures, the methods described here enable automated isolation of multiple analytes in a single integrated process chain. The products of the process are multiple isolates, each containing only a single defined class of analytes.

Examples of the disclosure thus provide methods for isolating two or more analyte classes from a single sample volume in a combined, integrated process in a centrifugal microfluidic cartridge as well as fluidics modules in the form of rotating bodies and devices configured to perform such methods. The aim is to save sample material and time and to minimize manual and instrumentation effort while at the same time isolating as many analytes as possible in high purity for subsequent analyses.

FIG. 1 schematically shows an example of a fluidics module 10 according to the present disclosure, which is configured to perform a method for isolating two analyte classes as described herein. The fluidics module 10 may be, for example, a rotary body rotatable about a center of rotation R or a fluidics module insertable into such a rotary body. The fluidics module 10 has fluidics structures comprising a first isolation chamber 12 and a second isolation chamber 14. The first isolation chamber 12 includes a first isolation structure 16. The second isolation chamber 14 includes a second isolation structure 18. A sample volume is guided into the first isolation chamber 12, as shown by an arrow 20 in FIG. 1. For this purpose, the fluidics structures have a first fluid line 22. Analytes of the first analyte class are retained by the first isolation structure 16, while analytes of the second analyte class are not retained by the first isolation structure 16, but pass through the first isolation structure 16 as part of a residual liquid. The residual liquid is guided into the second isolation chamber 14 through a second fluid line 24, which connects the first isolation chamber 12 to the second isolation chamber 14, as shown by an arrow 26 in FIG. 1. The analytes of the second analyte class are retained by the second isolation structure 18.

The analytes of the first analyte class are separated from the first isolation structure 16 and the analytes of the second analyte class are separated from the second isolation structure 18. This is shown by arrows 28 and 30 in FIG. 1. As a result, the analytes of the first analyte class and the analytes of the second analyte class are provided separately from each other for subsequent analysis. The separation 28 of the analytes of the first analyte class by the first isolation structure may, for example, comprise guiding the analytes of the first analyte class into a first collection chamber 32. The first collection chamber 32 may be connected to the first isolation chamber 12 via a fluid line for this purpose. Separating 30 the analytes of the second analyte class from the second isolation structure 18 may comprise guiding the analytes of the second analyte class into a second collection chamber, which is connected to the first collection chamber via a fluid line. The first collection chamber 32, the second collection chamber 34 and fluid lines connecting the same to the first isolation chamber 12 and the second isolation chamber 14, respectively, may be part of the fluidics structures of the fluidics module 10. The first collection chamber 32 is thus configured to receive analytes of the first analyte class detached from the first isolation structure 16, and the second collection chamber 34 is configured to receive analytes of the second analyte class detached from the second isolation structure 18.

In examples of the method described, the order in which the steps of separating the analytes of the first analyte class from the first isolation structure and guiding the residual liquid into the second isolation chamber take place is irrelevant. In examples, the residual liquid may first be guided into the second isolation chamber before the analytes of the first analyte class are separated from the first isolation structure. In examples of the present disclosure, the first isolation structure is configured to perform filtration based on size differences. In examples, the first isolation structure 16 is a filter having a pore size in a range of 20 nanometers to 200 nanometers, advantageously in a range of 20 nanometers to 45 nanometers. Thus, the first isolation structure enables isolating analytes of the first analyte class, i.e. extracellular vesicles and/or circulating tumor cells. Alternatively, thrombocytes could also be isolated by such filtration.

In examples, the first isolation structure has capture structures configured to bind analytes of the first analyte class. Such capture structures can be, for example, antibodies or aptamers. Alternatively, affinity-based methods may be used, for example peptides on magnetizable particles which bind components of the EV membrane. In examples, the first isolation structure may be configured to cause polymer precipitation. A polymer is added to form a lattice in which the EVs or circulating tumor cells (CTCs) are captured. Sedimentation can then be carried out to separate the lattice, i.e. to separate the analytes of the first analyte class from the first isolation structure.

In examples, separating the analytes of the first analyte class from the first isolation structure may comprise washing the analytes retained at the first isolation structure using a wash solution, eluting the analytes from the first isolation structure using an elution solution, and transferring the analytes detached from the first isolation structure to a first collection chamber. Thus, examples allow isolation and separation of the analytes of the first analyte class in a conventional manner.

In examples, the first isolation structure has a volumetrically defined chamber geometry of the first isolation chamber for sedimentation of analytes of the first analyte class. The geometrically defined chamber geometry can, for example, be provided by a channel which opens into the first isolation chamber at a certain radial height. Rotation can cause sedimentation in the first isolation chamber, through which the analytes of the first analyte class enter the chamber area, which lies radially outside the channel opening into the chamber. The residual liquid can then be guided into the second isolation chamber by drawing off the supernatant via the channel opening into the first isolation chamber at the specified radial height. In this case, the first isolation structure is formed by the lower part of the first isolation chamber. In examples, EVs can be sedimented in a polymer forming the first isolation structure, whereupon the supernatant can be removed, a dissolving buffer can be added to redissolve the polymer, and then the solution containing the EVs can be transferred. In such a case, the channel for withdrawing the supernatant may be located at the radially outer end of the first isolation chamber to withdraw the residual liquid, leaving the polymer with the analytes of the first analyte class in the first isolation chamber.

In examples, the isolation structures, in particular the second isolation structure, can be a surface for binding analytes. The surface can be formed by particles, columns, a membrane or a surface of the fluidics module. Such an isolation structure can effect solid phase isolation (bind, wash, elute) due to controlled binding conditions to a surface, for example isolation of cell-free nucleic acids or isolation of proteins. The surface can be part of the fluidics module, the cartridge, for example a channel or a chamber, or can be a body inserted into the fluidics module or a plurality of bodies inserted into the fluidics module, for example column/membrane or beads/nanoparticles).

In examples, the first or second isolation structure may comprise a surface for binding analytes formed by particles, for example beads, the particles being magnetizable, the method comprising rotating the fluidics module to move the magnetizable particles in the second isolation chamber by means of one or more stationary or movable magnets of a processing apparatus to assist mixing of the particles with the liquid in the respective chamber, for example with the residual liquid. In examples, the magnets may not only be used for mixing, but may also be configured to retain particles in the second isolation chamber when the elution liquid is transferred to the collection chamber with the analyte. Thus, in examples, one or more magnets may be stationary or movable outside the second isolation chamber to assist in retaining the magnetizable particles in the second isolation chamber when the analytes of the second analyte class are transferred to the second collection chamber.

Examples of the present disclosure provide a centrifugal microfluidic device comprising a fluidics module as described herein, and a processing apparatus configured to impart rotation to the fluidics module. The processing apparatus may include one or more stationary or movable magnets which move magnetizable particles in the second isolation chamber upon actuation of the fluidics module, i.e. upon rotation thereof, to assist in mixing the particles in the residual liquid.

In examples of the methods disclosed herein, isolating the analytes of the second analyte class comprises mixing the sample volume with a binding buffer, contacting the resulting mixture with a surface to bind the analytes of the second analyte class to the surface, washing the surface with the bound analytes using a wash buffer, eluting the analytes from the surface using an elution buffer, and transferring the analytes detached from the second isolation structure to a second collection chamber. In examples, a comparable method can be used to isolate the analytes of the first analyte class from the sample volume, wherein the detached analytes can be transferred to a first collection chamber. Examples thus enable isolation of the analytes of the first and/or second analyte classes using common bind-wash-elute methods.

In examples of the present disclosure, analytes can be isolated from the sample volume by means of centrifugation. By such centrifugation, further separation of the sample based on in differences density can be realized before, between or after filtration, for example for blood-plasma separation or for isolation of thrombocytes. Examples of the present disclosure are configured to extract analytes of two or more analyte classes from the sample volume. If three or more analytes are to be isolated, the fluidics structures are configured accordingly and have at least one further isolation chamber with at least one further isolation structure and at least one further collection chamber. The various analyte classes can then be removed from the various collection chambers of the fluidics module, the microfluidic cartridge, for analysis.

In examples, the fluidics module comprises at least one filter which is fluidically connected to the input side of the first isolation chamber, which is permeable to the analytes of the first analyte class and the analytes of the second analyte class, and which is configured to filter cells, cell fragments, particles and contamination from the sample volume. Accordingly, examples of the method comprise guiding the sample volume through a corresponding upstream filter prior to guiding the sample volume into the first isolation chamber. Thus, examples enable preparation of the sample volume for subsequent isolation of the analytes of the first analyte class and second analyte class from the sample volume.

In examples of the present disclosure, preparing the biological sample comprises one or more of the following processes:

- Performing blood-plasma separation of the biological sample to obtain plasma from which the sample volume is recovered.
- Performing blood-plasma separation of a coagulated biological sample to obtain serum from which the sample volume is recovered.
- Performing thrombocyte isolation of the plasma to obtain thrombocyte-poor plasma from which the sample volume is recovered.
- Performing thrombocyte isolation of the plasma to obtain thrombocyte-rich plasma from which the sample volume is recovered.
- Performing enzymatic digestion to decompose proteins and protein aggregates in the biological sample to recover the sample volume.
- Performing liquefaction and/or homogenization of the biological sample to recover the sample volume.

In examples, the fluidics module has fluidics structures configured to perform one or more of the aforementioned processes.

For example, thrombocyte isolation can be performed by means of sedimentation, wherein the sediment corresponds to thrombocyte-rich plasma and the supernatant corresponds to thrombocyte-poor plasma. Depending on whether the sample volume is taken by means of a channel at a radially lower end or a radially lateral end of the sedimentation chamber, thrombocyte-poor or thrombocyte-rich plasma can thus be obtained. Furthermore, thrombocyte isolation can be achieved by means of filtration in that the fluidics module has a filter whose pore size is configured to retain the thrombocyte. The filtrate would then be thrombocyte-poor and the retentate or eluate subsequently detached from the filter would be thrombocyte-rich. The size of thrombocytes is approx. 1 to 4 μm. It is known, for example, to use filters with a corresponding pore size, such as a pore size of 600 nanometers, to retain thrombocytes.

In examples of the present disclosure, the first isolation structure is configured to retain EVs and/or CTCs, wherein separating the analytes from the first isolation structure comprises separating the EVs and/or CTCs as a whole or separated into their constituent parts from the isolation structure. In examples, EVs/CTCs may be separated while leaving the cfDNA in the flow-through by one of the following methods:—filtration,—methods where the analytes are captured, using, for example, antibodies, aptamers or affinity-based methods, such as peptides on magnetizable particles which bind components of the EV membrane;—polymer precipitation, where a polymer is added which forms a lattice in which the EVs/CTCs are captured, followed by sedimentation to separate the lattice;—sedimentation to isolate CTCs from the sample volume.

In general, in examples of the method described herein, a sample with a volume of a few microliters to several milliliters can be transferred automatically or manually into the fluidics module (the microfluidic cartridge). The fluidics module is then automatically processed further in an apparatus. Analytes of several analyte classes are successively isolated from the sample in a single process using various methods. To this end, the apparatus may be configured to subject the fluidics module to rotations by which the various liquids are moved through the fluidics structures as described herein. In examples, the fluidics module may be subjected to a corresponding frequency protocol so that the liquids in the cartridges may be moved by the centrifugal force. The fluidics structures may also be configured to support the handling of the liquids by other processes, such as hydrodynamic processes. The sample is not divided up for the respective isolation methods, but is automatically passed on by means of microfluidic connection channels so that the respective analytes are isolated from the complete sample volume.

Figure 2:
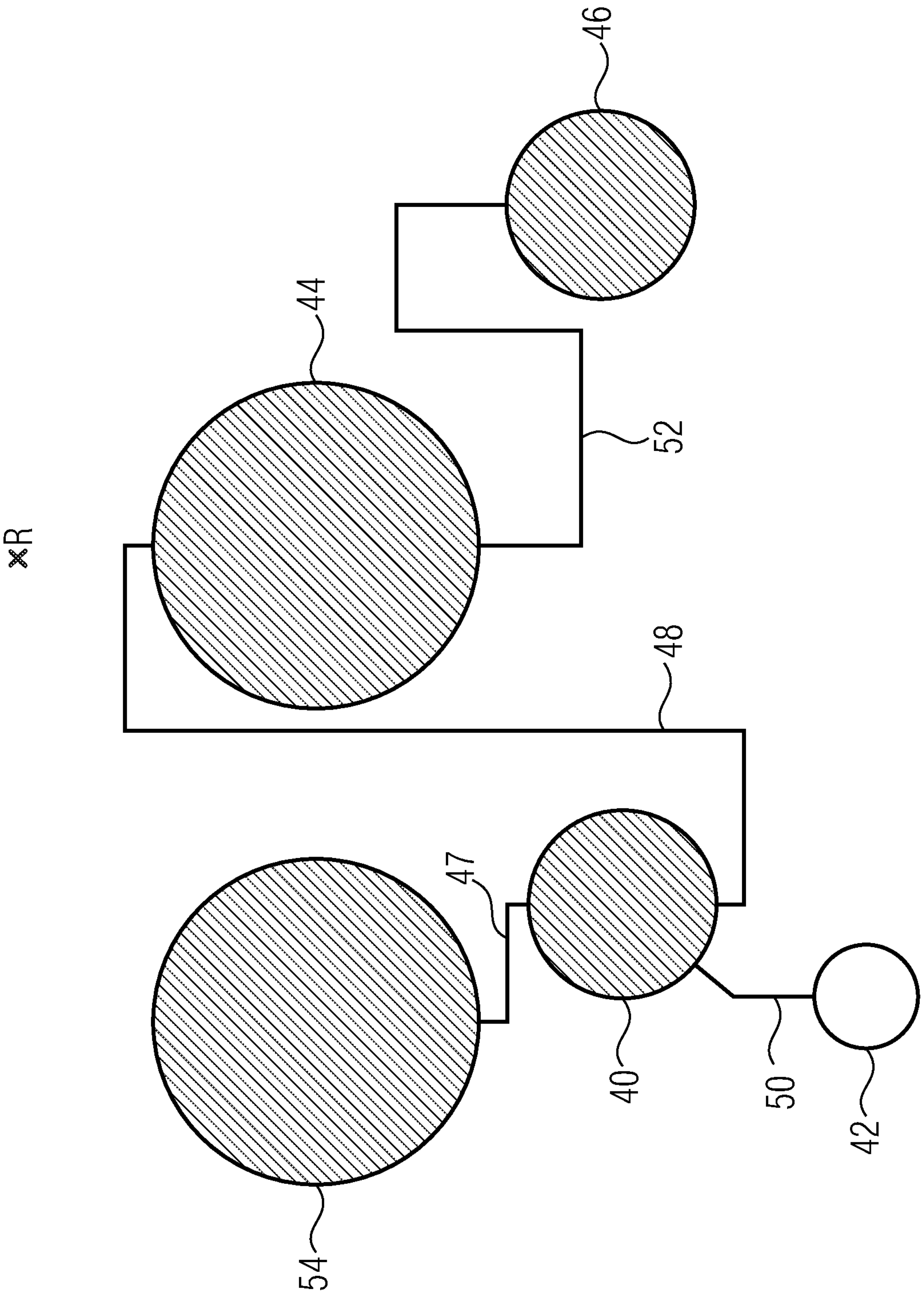
FIG. 2 shows a schematic representation of components of a fluidics module according to an example of the present disclosure.

FIG. 2 schematically shows components of a fluidics module according to an example of the present disclosure. The components comprise a first filter structure 40, which represents a first isolation structure, a first capture structure 42, which represents a first collection chamber, a separation structure 44, which represents a second isolation structure, and a second capture structure 46, which represents a second collection chamber. A first fluid line 47 leads to the first filter structure 40, a second fluid line 48 connects the filter structure 40 to the separation structure 44, a third fluid line 50 connects the first capture structure 42 to the filter structure 40 and a fourth fluid line 52 connects the second capture structure 46 to the separation structure 44. As shown in FIG. 2, in examples, a further filter structure 54 can optionally be connected upstream, which has a pore size allowing extracellular vesicles, circulating tumor cells and cell-free nucleic acids to pass through. The first filter structure 40 is configured to retain extracellular vesicles and allow cell-free nucleic acids to pass through. In examples, the first filter structure may be configured to retain circulating tumor cells. In alternative examples, the first filter structure may be replaced by an isolation structure configured to retain circulating tumor cells by sedimentation.

Figure 3:
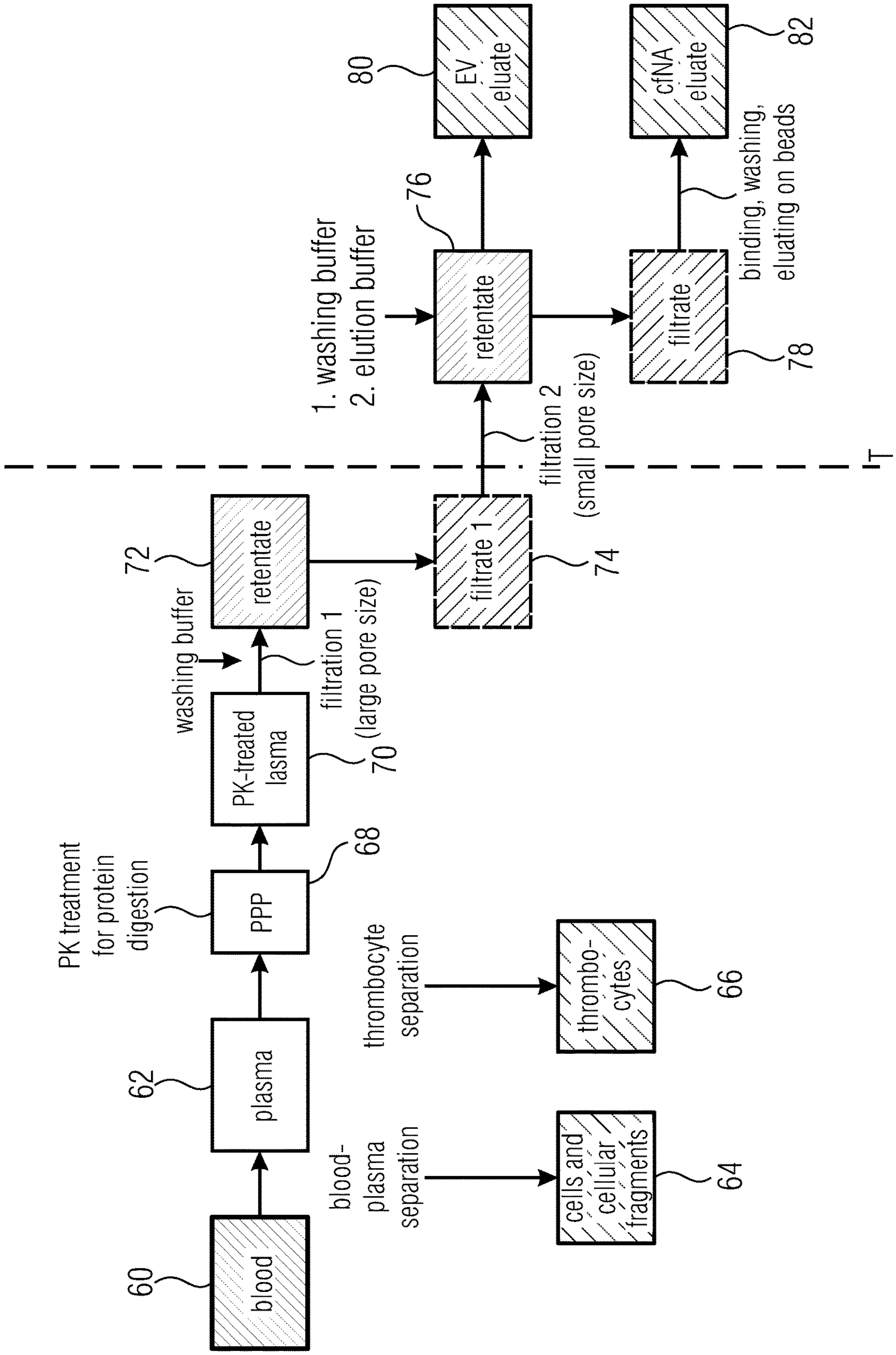
FIG. 3 shows a diagram schematically showing a method according to the present disclosure.

With reference to FIG. 3, a possible implementation of a procedure for the purification of several analytes from one sample volume is explained below. In FIG. 3, the steps which actually concern the method for isolating two different analyte classes from a sample volume are shown to the right of a dividing line T, while a method for preparing the sample volume is shown to the left of the dividing line T. Examples of fluidics modules of the present disclosure have fluidics structures to perform the method shown in FIG. 3. However, the method need not have all of the processes shown in FIG. 3, and in particular the process steps shown to the left of the dividing line T may be considered optional in whole or in part.

A blood sample is transferred to the fluidics module, 60. A blood-plasma separation is performed to obtain plasma, 62, wherein cells and cellular fragments are separated, 64. Subsequently, a thrombocyte separation can be performed to separate thrombocytes from the plasma, 66. Subsequently, protein digestion by proteinase K (PK) can be performed for protein digestion, 68, thereby obtaining PK-treated plasma, 70. The plasma thus obtained may now be subjected to coarse filtration with a large pore size, for example by a filter structure 54 as shown in FIG. 2. This filtration, referred to as filtration 1 in FIG. 3, produces a retentate 72 and a filtrate 74. The filtrate 74 represents the sample volume of the biological sample from which at first EV and then NA are isolated. In the example shown, the primary separation is carried out by means of filtration, which is referred to as filtration 2 in FIG. 3. In this process, the optionally previously prepared sample is pressed through one or more filter membranes using centrifugal forces. The filter membranes can be made of different materials and have different pore sizes, for example between 20 nm and 10 μm. Potential materials for the membranes are polyester (PES), recycled material (RC), anodized aluminum oxide (AAO) or TEPC (fabric-equivalent material). If several filter membranes are used, the sample is pressed through the different filter membranes one after the other, at first filter membranes with a larger pore diameter and then filter membranes with a smaller pore diameter. For example, matrix components, such as cells, cell fragments or protein aggregates, with a large diameter can be separated by the upstream filtration 1, while EV and cfNA pass through the filter, for example the additional filter structure 54 in FIG. 2. The final filter, which represents the first isolation structure, has a pore size such that smaller contaminants, for example individual proteins, and the cfNA pass through the membrane, but EVs are retained. This filtration is referred to as filtration 2 in FIG. 3. This filtration 2 produces a retentate 76 and a filtrate 78. The filtrate 78 represents the residual liquid which is guided to the second isolation structure.

To further deplete the matrix components in the retentate 76, washing steps can be carried out using aqueous solutions, wash buffers. The EV purified in this way can then be separated from the filter for further analysis by means of an elution buffer and transferred to a collection chamber of the fluidics module as EV eluate 80. The flow through the filter, i.e. the filtrate 78, contains the cfNA, apart from the remaining sample matrix, which may now be concentrated and purified using further methods. Various methods are available for this on centrifugal microfluidic cartridges, the fluidics module, for example cfNA solid phase isolation on beads. In such solid phase isolation, cfNA is bound to beads, then washed using a wash buffer and eluted using an elution buffer and transferred to a collection chamber of the fluidics module as cfNA eluate 82. Thus, analytes of the first analyte class and analytes of the second analyte class are provided separately from each other for subsequent analysis.

In examples where the second isolation structure can be moved out of the second isolation chamber, after separating the analytes of the second analyte class from the second isolation structure, the second isolation structure can be moved out of the second isolation chamber while the analytes of the second analyte class remain in the second isolation chamber. In the above example, for example, the solid phase matrix in the form of the beads could be transferred out of the isolation chamber after elution, while the eluate remains in the isolation chamber.

As already explained above, blood plasma separation can optionally be performed upstream for blood samples using the centrifugal forces in the centrifugal microfluidic system. On the one hand, this can further reduce the manual effort entailed for sample preparation and, on the other hand, further increase the reproducibility of the entire analytical process. In contrast to manual blood-plasma separation, a centrifugal pneumatic operation can be used to remove the plasma supernatant after centrifugation of whole blood under rotation, which practically eliminates re-sedimentation effects. A further aim of an integrated, upstream blood-plasma separation may be the automatically achieved isolation of cells and cell fragments, which can be regarded as a further class of analytes. In addition to the analysis of healthy cells, the analysis of disease-associated cells, such as circulating tumor cells, CTCs, can be of particular relevance.

In examples, the sedimentation of circulating tumor cells is not a pretreatment of the biological sample, but an isolation of analytes of the second analyte class. In other examples, the isolation of the circulating tumor cells represents the isolation of analytes of a third analyte class, which precedes the isolation of EV as analytes of a first analyte class and the isolation of cfNA as analytes of a second analyte class.

In analogy to blood-plasma separation, plasma can be separated into thrombocyte-rich plasma (PRP=Platelet Rich Plasma) and thrombocyte-poor plasma (PPP=Platelet Poor Plasma) by using the inherent centrifugal force and removing the supernatant once or several times. The PRP generated in this way can be removed from the cartridge as an isolate for the analysis of thrombocytes and used, for example, for the analysis of tumor educated platelets (TEP). The generated PPP, however, can go to the further process of successive isolation of the analyte classes EV and cfNA. If cell-free DNA of mitochondrial origin (cf-mtDNA) is to be analyzed, such upstream thrombocyte isolation may be essential to prevent or minimize contamination of the cell-free mitochondrial DNA with mitochondrial DNA from lysed thrombocytes (mtDNA). TEPs can be regarded as analytes of a third analyte class, which are removed from the sample volume before the analytes of the first and second analyte classes.

Furthermore, optionally and depending on the matrix, the biological sample can be liquefied and/or homogenized before filtration, for example in the case of sputum or stool samples, or enzymatic digestion with protease (e.g. proteinase K) can be carried out. This decomposes proteins and protein aggregates which make it difficult to isolate the analytes, for example by clogging the filter membranes or binding nucleic acids. The enzymes can be separated from the analytes again by washing steps, for example the wash buffer indicated in FIG. 3, or solid phase isolation (bind-wash-elute), so that they do not impede further analyses.

Figure 4:
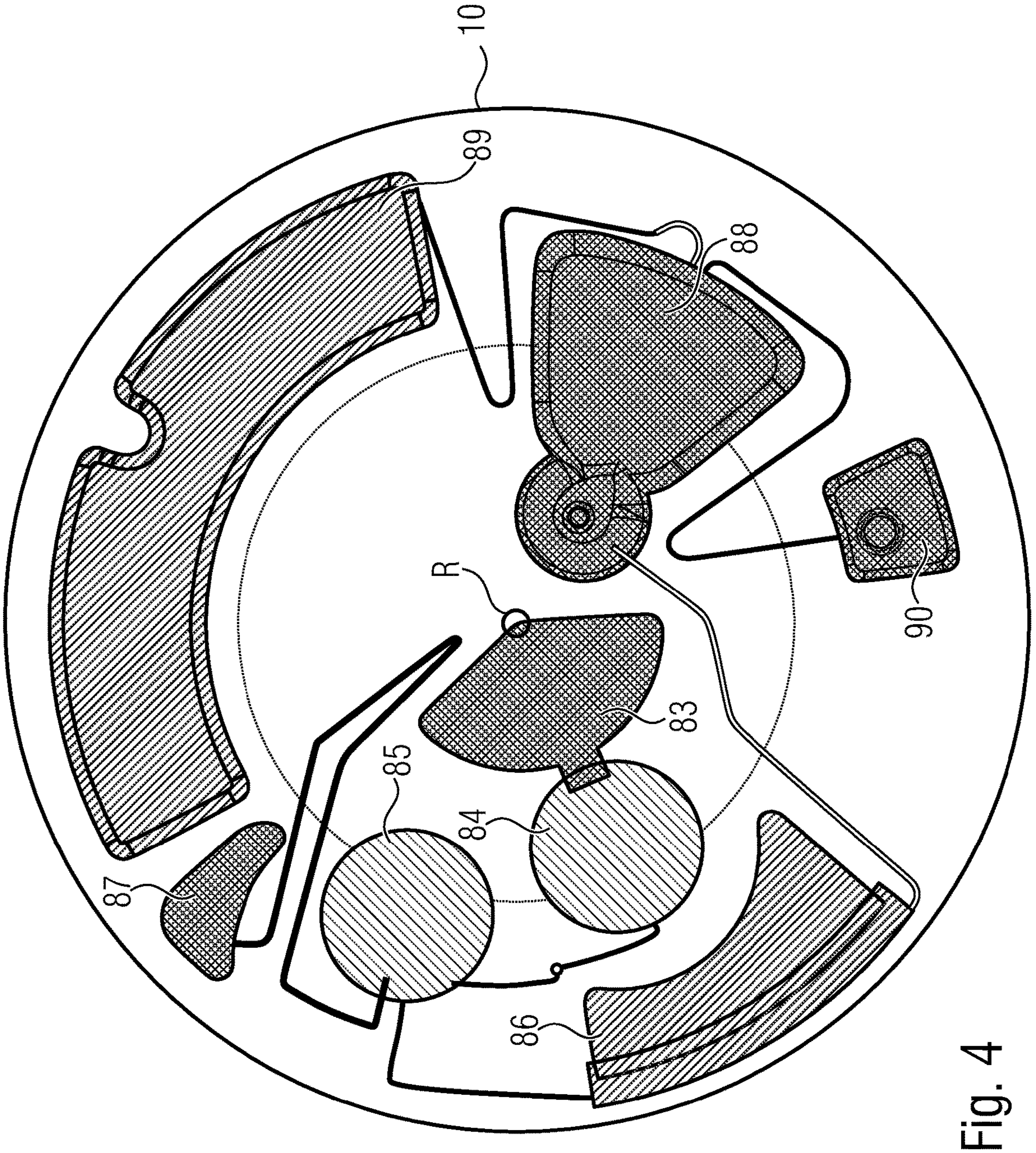
FIG. 4 shows a schematic representation of a fluidics module in the form of a centrifugal microfluidic cartridge according to an example of the present disclosure.

FIG. 4 schematically shows a fluidics module 10 in the form of a rotating body 10 rotatable about a center of rotation R, which has fluidics structures configured to perform automated, combined isolation of cfNA and EV from a single sample volume in the form of a human plasma sample. Fluidics structures formed in the fluidics module include a sample inlet chamber 83, a pre-filtration chamber 84, a filtration chamber 85 for EV isolation, a chamber 86 for collecting the filtrate from the filtration chamber 85, a collection chamber 87 for removing the EV isolate, a chamber 88 for solid phase isolation of cfNA, a collection chamber 89 for wash fluids of the solid phase isolation, and a collection chamber 90 for removing the cfNA isolate. As shown in FIG. 4, the respective chambers are connected to one another by fluid lines. The fluid lines are implemented to allow transfer of liquid between the respective chambers utilizing centrifugal force and possibly other effects, such as hydrodynamic effects. The filtration chamber 85 for EV isolation represents a first isolation chamber as described herein and the chamber 88 represents a second isolation chamber as described herein.

A filter membrane can separate an inlet-side section of the fluid chamber, in which the filter membrane is arranged, from an outlet-side section of this fluid chamber. In examples, the inlet-side section of the fluid chamber and the outlet-side section of the fluid chamber are arranged one above the other in the direction of an axis of rotation passing through the center of rotation.

During operation, the plasma sample is fed into the sample inlet chamber 83 and then filtered sequentially through the filter membranes arranged in the chambers 84 and 85. The filter membrane arranged in the chamber 84 has larger pore diameters than the filter membrane arranged in the chamber 85 so that the analytes of the first and second analyte classes may pass through, but larger matrix components are retained. The second filter membrane in the chamber 85 is designed so that cfNA may pass through, but EV is retained. This allows both analytes to be separated from the sample without loss. The cfNA filtrate is collected in the chamber 86 and transferred from there to the chamber 88 for solid phase isolation. Alternatively, the filtrate could also be transferred directly to the chamber for solid phase isolation. The EVs retained on the second filter membrane in chamber 85 are then washed with aqueous buffer solutions, which may be added manually or automatically to chamber 83 to remove matrix components which may pass through the filters. The wash solutions can then be collected in the chamber 86 after transferring the cfNA filtrate to the chamber 88. After washing the EVs, they are transferred from the filter in the chamber 85 to the collection chamber 87, from which they can be removed manually or automatically. The filtrate with the cfNA is subjected to solid phase isolation in the chamber 88 by bringing it into contact with a surface. In examples, solid phase isolation is carried out according to the bind-wash-elute method using magnetic or magnetizable particles with which the filtrate is brought into contact, which bind the NA via a silica surface. Matrix components, such as proteins, can be removed in one or more washing steps with solvent-containing liquids. The washing solutions are collected in the chamber 89. After washing, the cfNAs are eluted from the magnetizable particles using an aqueous elution buffer and then transferred to the chamber 90 for removal.

Compared to the known technology in serial single procedures, where, for example, isolation of extracellular vesicles takes place by filtration in a first apparatus, then a manual transfer and a subsequent isolation of nucleic acids by solid phase isolation in a second apparatus, the combination method presented herein allows the isolation of different analytes not only in a single apparatus, a centrifugal microfluidic processing apparatus, but also in a single consumable, namely a fluidics module in the form of a centrifugal microfluidic cartridge. In addition to the advantages of easy handling and lower material and personnel costs, this integrated process chain is expected to have an advantageous effect on the reproducibility of the isolation. This aspect is highly relevant as pre-analytical variations are considered a major obstacle in the clinical translation of circulating analytes. In contrast to the known technology in combination methods, the presented method allows the isolation of different analyte classes from a single sample volume without negatively influencing the respective analytes. Specifically, in the method described herein, the analyte class of extracellular vesicles can be separated from the analyte class of nucleic acids and isolated from the sample matrix without destroying, damaging or minimizing either analyte class to a significant extent. The resulting high-quality isolates of the respective analyte classes allow precise and reproducible analyses at single and multi-analyte level to increase sensitivity and specificity without an undesirable increase in sample volume.

Figure 5A:
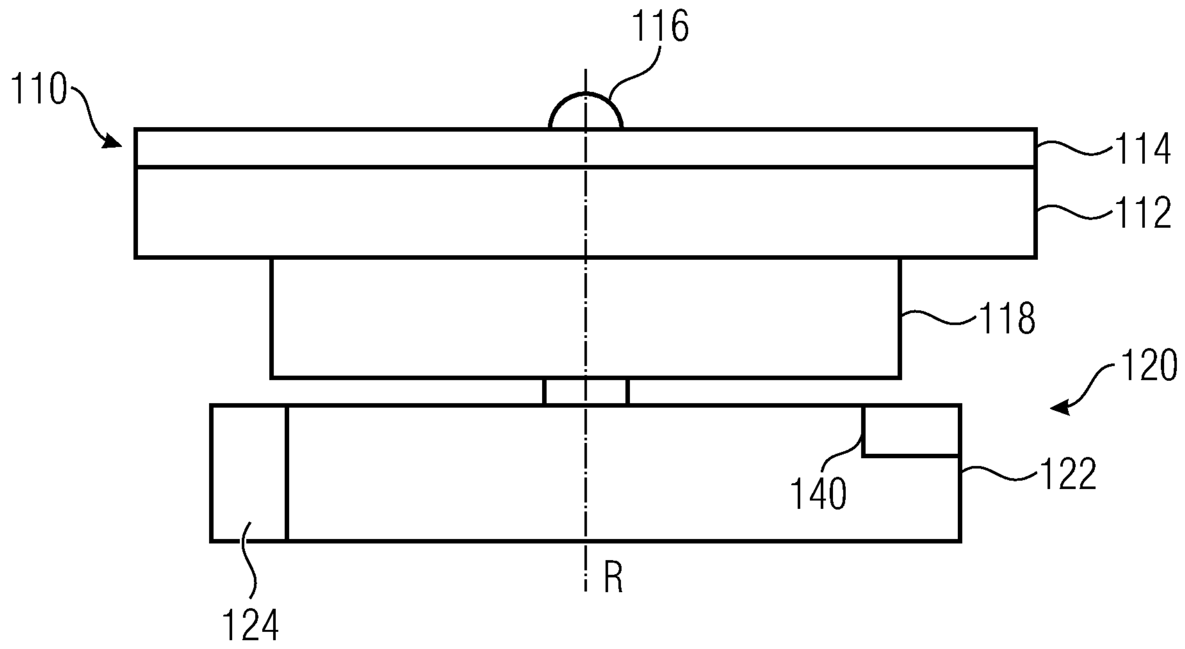
FIGS. 5A and 5B show schematic representations of devices utilizing fluidics modules as described herein.
Figure 5B:
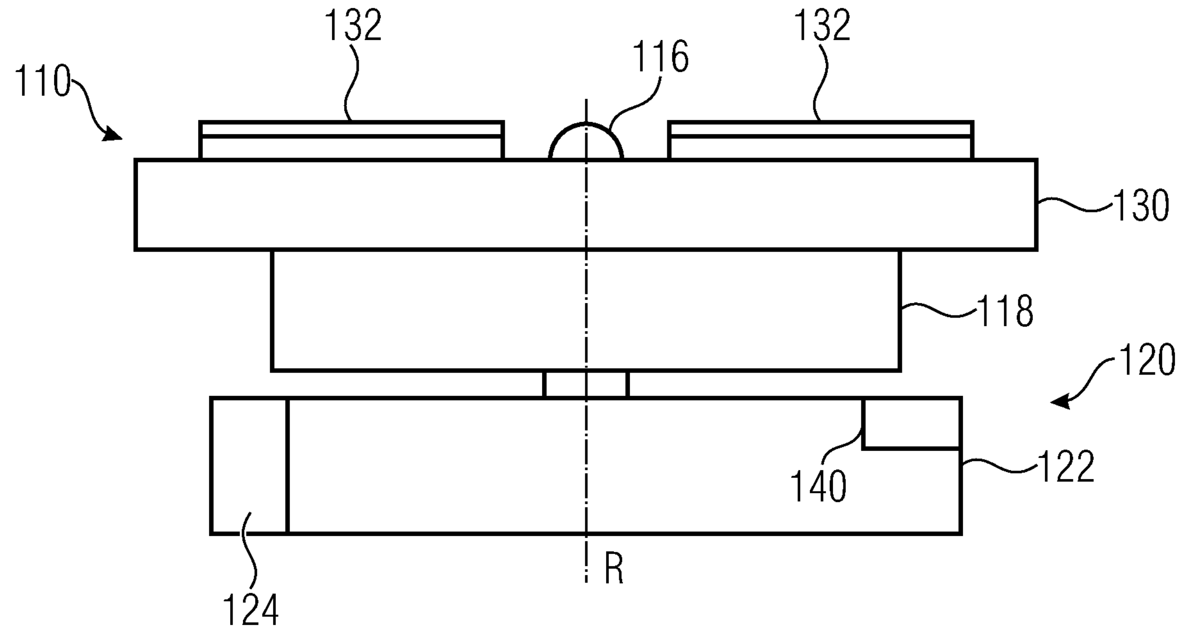

Referring to FIGS. 5A and 5B, examples of centrifugal microfluidic systems are described, utilizing or comprising a fluidics module as described herein. In other words, the fluidics module in the systems of FIGS. 5A and 5B may be any of the fluidics modules described herein.

FIG. 5A shows a device with a fluidics module 110 in the form of a rotating body having a substrate 112 and a cover 114. The substrate 112 and the cover 114 may be circular in plan view, with a central opening through which the rotating body 110 can be attached to a rotating part 118 of a drive device 120 via a conventional attachment device 116. The rotating part 118 is rotatably mounted on a stationary part 122 of the drive device 120. The drive device 120 may be, for example, a conventional centrifuge, which may have an adjustable rotational speed, or a CD or DVD drive. A control device 124 may be provided, which is configured to control the drive device 120 to impart rotation or rotations of different rotational frequencies to the rotating body 110. The control device 124 may, as will be apparent to those skilled in the art, be implemented by, for example, an appropriately programmed computing device or a user-specific integrated circuit. The control device 124 may further be configured to, in response to manual input from a user, control the drive device 120 to effect the used rotations of the rotational body. In either case, the control device 124 may be configured to control the drive device 120 to impart the used rotation to the rotational body to implement embodiments of the invention as described herein. The drive device 120 may be a conventional centrifuge having only one direction of rotation.

The rotating body 110 has the used fluidics structures. The used fluidics structures may be formed by cavities and channels in the cover 114, the substrate 112, or in the substrate 112 and the cover 114. In embodiments, for example, fluidics structures may be formed in the substrate 112, while fill openings and vent openings are formed in the cover 114. In embodiments, the structured substrate (including fill openings and vent openings) is arranged at the top and the cover is arranged at the bottom.

In an alternative embodiment shown in FIG. 5B, fluidics modules 132 are inserted into a rotor 130 and together with the rotor 130 form the rotating body 110. The fluidics modules 132 may each have a substrate and a cover, in which in turn corresponding fluidics structures may be formed. The rotating body 110 formed by the rotor 130 and the fluidics modules 132 in turn may be subjected to rotation by a drive device 120 controlled by the control device 124.

In FIGS. 5A and 5B, the center of rotation about which the fluidics module or the rotational body is rotatable is again referred to by R.

The device shown in FIGS. 5A and 5B represents a processing apparatus configured to impart rotations to the fluidics module as used to perform the methods described herein. The processing apparatus may include one or more stationary or movable magnets 140 configured to assist in mixing particles with the residual liquid in the second isolation chamber. To this end, the magnets 140 may be positioned at a suitable location of the stationary portion of the drive device 120, which passes through the second isolation chamber so that the magnetic field thereof can act on magnetizable particles in the second isolation chamber.

In embodiments of the invention, the fluidics module or rotating body comprising the fluidics structures may be formed from any suitable material, for example plastic such as PMMA (polymethyl methacrylate), PC (polycarbonate), PVC (polyvinyl chloride) or PDMS (polydimethylsiloxane), glass or the like. The rotating body 110 may be considered to be a centrifugal microfluidic platform. In embodiments, the fluidics module or rotating body may be formed from a thermoplastic, such as PP (polypropylene), PC, COP (cyclic olefin polymer), COC (cyclo olefin copolymer) or PS (polystyrene).

The fluidics modules described herein thus allow several analyte classes to be isolated from an identical sample volume and removed from the process in separate isolates. Until now, to generate several isolates with only one analyte class each, either the sample was fractionated into several sub-volumes, resulting in a loss of sensitivity, or a larger sample volume was fractionated to achieve the same sensitivity, which is not feasible in practice due to the burden for patients or limited sample resources. There is no known technology in centrifugal microfluidics which offers all the principles for realization the isolation of different analyte classes (centrifugation, removal of supernatant, single and multi-stage filtration and solid phase isolation) and allows their combination in integrated, automated process chains. In particular, it was surprisingly recognized that the individual steps of the process chain presented here, namely EV filtration and cfNA solid phase isolation as well as various optional steps, do not negatively influence one another to a significant extent. For example, it was surprisingly recognized that the purification of EV by means of filtration does not result in a significant loss in cfNA due to absorption on the filter surface or in the filter volume.

Examples of the present disclosure provide a rotating body integrating one or more series-connected filter structures for filtering, which can be flowed through by means of centrifugal force and whose filter pores have a diameter between 20 nm and 200 nm, and in which a collecting structure for the flow-through is provided. The collection structure may contain an isolation structure to mix the flow-through with a buffer and subsequently bring the buffer-flow-through mixture into contact with an (active) surface to bind nucleic acids at this surface. Furthermore, the rotating body may have an integrated further fluidic structure to collect the buffer-flow-through mixture from the separation structure in the further fluidic structure, and also to collect at least one wash buffer which washes the (active) surface. In examples, the (active) surface may be formed from magnetic or magnetizable particles. In examples, a magnet may be integrated into the apparatus for applying the rotation, which can be movable and can support mixing of the beads with the liquid. In examples, the active surface may be a silica membrane.

In examples, the second isolation structure as described herein may be a separation structure as described in DE 10 2018 219 091 A1. In examples, the first and second isolation structures may be formed by isolation structures as known per se and described at the beginning.

No separate explanation is required that chambers described herein, such as isolation chambers and fluid chambers, can each have several chamber sections or can be formed by several chambers. Chambers, for example fluid chambers or isolation chambers, which are connected via a fluid line, do not have to be connected directly via the fluid line, but further fluid chambers can be arranged in between.

Although features of the invention have each been described in terms of device features or method features, it is obvious to those skilled in the art that corresponding features may also be part of a method or device. Thus, the device may be configured to perform corresponding method steps, and the respective functionality of the device may represent corresponding method steps.

In the above detailed description, various features have been partly grouped together in examples to rationalize the disclosure. This type of disclosure is not to be interpreted as intending the claimed examples to have more features than are expressly stated in each claim. Rather, as the following claims reflect, subject-matter may lie in fewer than all the features of a single disclosed example. Consequently, the following claims are hereby incorporated into the detailed description, wherein each claim may stand as its own separate example. While each claim may stand as its own separate example, it should be noted that although dependent claims in the claims refer back to a specific combination with one or more other claims, other examples also include a combination of dependent claims with the subject-matter of any other dependent claim or a combination of any feature with other dependent or independent claims. Such combinations are included unless it is stated that a specific combination is not intended. Furthermore, a combination of features of a claim with any other independent claim is intended to be also encompassed, even if that claim is not directly dependent on the independent claim.

While this invention has been described in terms of several embodiments, there are alterations, permutations, and equivalents which fall within the scope of this invention. It should also be noted that there are many alternative ways of implementing the methods and compositions of the present invention. It is therefore intended that the following appended claims be interpreted as including all such alterations, permutations and equivalents as fall within the true spirit and scope of the present invention.

The invention claimed is:

1. A method for isolating analytes of a first analyte class, which are extracellular vesicles and/or circulating tumor cells, and analytes of a second analyte class, which are cell-free nucleic acids, from the same sample volume of a biological sample in a centrifugal microfluidic system, comprising a fluidics module comprising a first isolation chamber comprising a first isolation structure and a second isolation chamber comprising a second isolation structure, comprising:

- guiding the sample volume into the first isolation chamber so that the analytes of the first analyte class are retained by the first isolation structure, while the analytes of the second analyte class are not retained by the first isolation structure and pass through the first isolation structure as part of a residual liquid;
- guiding the residual liquid into the second isolation chamber so that the analytes of the second analyte class are retained by the second isolation structure; and
- separating the analytes of the first analyte class from the first isolation structure and separating the analytes of the second analyte class from the second isolation structure to provide the analytes of the first analyte class and the analytes of the second analyte class separately from each other for subsequent analysis, wherein the first isolation structure is a filter comprising a pore size in a range from 20 nanometers to 200 nanometers, wherein the second isolation structure is a surface for binding analytes, wherein the surface is formed by particles, and wherein the particles are magnetizable, the method comprising rotating the fluidics module to, by means of one or more stationary or movable magnets of a processing apparatus, move the magnetizable particles in the second isolation chamber to assist mixing of the particles with the residual liquid, and/or support retaining the magnetizable particles in the second isolation chamber during transfer of analytes of the second analyte class into the second collection chamber.

2. The method according to claim 1, comprising washing the analytes of the first analyte class retained at the first isolation structure by means of a washing solution, eluting the analytes from the first isolation structure by means of an elution solution and transferring the analytes detached from the first isolation structure into a first collection chamber.

3. The method according to claim 1, comprising mixing the sample volume with a binding buffer, bringing the resulting mixture into contact with the surface to bind the analytes of the second analyte class to the surface, washing the surface with the bound analytes using a wash buffer, eluting the analytes from the surface using an elution buffer, and transferring the analytes detached from the second isolation structure to a second collection chamber.

4. The method according to claim 1, comprising, prior to guiding the sample volume into the first isolation chamber, guiding the sample volume through an upstream filter which is permeable to the analytes of the first analyte class and the analytes of the second analyte class in order to filter cells, cell fragments, particles and impurities from the sample volume.

5. The method according to claim 1, comprising preparing the biological sample, wherein preparing comprises one or more of the following processes:

performing blood-plasma separation of the biological sample to acquire plasma from which the sample volume is recovered;

performing blood-plasma separation of a coagulated biological sample to acquire serum from which the sample volume is recovered;

performing thrombocyte isolation of the plasma to acquire thrombocyte-poor plasma from which the sample volume is recovered;

performing thrombocyte isolation of the plasma to acquire thrombocyte-rich plasma from which the sample volume is recovered;

performing enzymatic digestion to decompose proteins and protein aggregates in the biological sample to recover the sample volume; and performing liquefaction and/or homogenization of the biological sample to recover the sample volume.

6. The method according to claim 1, wherein the filter comprises a pore size in a range from 20 nanometers to 45 nanometers.

7. A centrifugal microfluidic device comprising a fluidics module for isolating analytes of a first analyte class, which are extracellular vesicles and/or circulating tumor cells, and analytes of a second analyte class, which are cell-free nucleic acids, from the same sample volume of a biological sample in a centrifugal microfluidic system, and a processing apparatus configured to subject the fluidics module to rotation, the fluidics module comprising:

a first isolation chamber comprising a first isolation structure;

a second isolation chamber comprising a second isolation structure;

a first fluid line for guiding the sample volume into the first isolation chamber so that the analytes of the first analyte class are retained by the first isolation structure, while the analytes of the second analyte class are not retained by the first isolation structure and pass through the first isolation structure as part of a residual liquid;

a second fluid line for guiding the residual liquid into the second isolation chamber so that the analytes of the second analyte class are retained by the second isolation structure;

a first collection chamber connected to the first isolation chamber for receiving analytes of the first analyte class detached from the first isolation structure; and a second collection chamber connected to the second isolation chamber for receiving analytes of the second analyte class detached from the second isolation structure or for receiving the second isolation structure from which the analytes of the second analyte class have been detached, wherein the first isolation structure is a filter comprising a pore size in a range from 20 nanometers to 200 nanometers, wherein the second isolation structure is a surface for binding analytes, wherein the surface is formed by magnetizable particles, and wherein the processing apparatus comprises one or more stationary or movable magnets which are arranged outside the second isolation chamber in order to support mixing of magnetizable particles with the filtrate during rotation of the fluidics module and/or in order to support retention of the magnetizable particles in the second isolation chamber during transfer of analytes of the second analyte class into the second collection chamber.

8. The centrifugal microfluidic device according to claim 7, wherein the fluidics module comprises at least one of the following:

fluidics structures configured to introduce a binding buffer into the second isolation chamber to support binding of the analytes of the second analyte class to the surface, fluidics structures configured to introduce a wash buffer for washing the surface with the bound analytes into the second isolation chamber, fluidics structures configured to introduce an elution buffer for eluting the analytes from the surface of the second isolation chamber, fluidics structures configured to receive the wash buffer after washing the surface with the bound analytes.

9. The centrifugal microfluidic device according to claim 7, wherein the fluidics module comprises at least one filter fluidically connected to the input side of the first isolation chamber, which is permeable to the analytes of the first analyte class and the analytes of the second analyte class and which is configured to filter cells, cell fragments, particles and impurities from the sample volume.

10. The centrifugal microfluidic device according to claim 7, wherein the fluidics module comprises at least one of the following:

fluidics structures configured to perform blood-plasma separation of the biological sample to acquire plasma from which the sample volume is recovered;

fluidics structures configured to perform blood-plasma separation of a coagulated biological sample to acquire serum from which the sample volume is recovered;

fluidics structures configured to perform thrombocyte isolation of the plasma to acquire thrombocyte-poor plasma from which the sample volume is recovered;

fluidics structures configured to perform thrombocyte isolation of the plasma to acquire thrombocyte-rich plasma from which the sample volume is recovered;

fluidics structures configured to perform enzymatic digestion to decompose proteins and protein aggregates in the biological sample to recover the sample volume; and fluidics structures configured to perform liquefaction and/or homogenization of the biological sample to recover the sample volume.

11. The centrifugal microfluidic device according to claim 7, wherein the filter comprises a pore size in a range from 20 nanometers to 45 nanometers.

* * * * *